United States Patent [19]

Findeisen et al.

[11] 4,242,489
[45] Dec. 30, 1980

[54] PROCESS FOR PREPARING POLYURETHANES

[75] Inventors: Kurt Findeisen; Kuno Wagner; Walter Uerdingen, all of Leverkusen, Fed. Rep. of Germany

[73] Assignee: Bayer Aktiengesellschaft, Leverkusen, Fed. Rep. of Germany

[21] Appl. No.: 47,517

[22] Filed: Jun. 11, 1979

Related U.S. Application Data

[62] Division of Ser. No. 656,909, Feb. 10, 1976, Pat. No. 4,173,567.

[30] Foreign Application Priority Data

Feb. 22, 1975 [DE] Fed. Rep. of Germany ....... 2507682

[51] Int. Cl.³ .................. C08G 18/77; C08G 18/14; C08G 18/78
[52] U.S. Cl. ...................................... 528/73; 528/59; 528/69; 427/385.5
[58] Field of Search ........................... 528/59, 69, 73; 427/385 R

[56] References Cited

U.S. PATENT DOCUMENTS

| | | | |
|---|---|---|---|
| 3,313,747 | 4/1967 | Schramm | 260/307 C |
| 3,591,590 | 7/1971 | Haug et al. | 548/312 |
| 3,641,199 | 2/1972 | Niederhauser et al. | 260/859 R |
| 3,681,377 | 8/1972 | Singhal | 548/312 |
| 3,792,023 | 2/1974 | Harenith et al. | 260/77.5 AQ |
| 3,839,354 | 10/1974 | Habermeier et al. | 548/312 |
| 3,953,432 | 4/1976 | Wehrmeister | 260/244 R |
| 3,963,679 | 6/1976 | Ullrich et al. | 260/75 NE |

OTHER PUBLICATIONS

Saunders et al., Polyurethanes, Part I, Interscience, N.Y. (1962) pp. 64–73.

*Primary Examiner*—H. S. Cockeram
*Attorney, Agent, or Firm*—Gene Harsh; Lawrence S. Pope; Thomas W. Roy

[57] ABSTRACT

The present invention relates to a new organic heterocyclic isocyanate which is the reaction product of an organic diisocyanate and an amino or hydroxy nitrile. The invention also relates to a process of producing such isocyanates by reacting an excess of the diisocyanate with the nitrile under conditions under which the nitrile will not decompose and then maintaining the reaction mixture at an elevated temperature until the isocyanate nitrile adduct cyclizes. The reaction may be carried out in the presence of a catalyst for isocyanate addition reactions. Additionally, the invention relates to a process for the production of polyurethane by the reaction of the heterocyclic isocyanates with compounds carrying at least two isocyanate reactive hydrogen atoms per molecule.

4 Claims, No Drawings

PROCESS FOR PREPARING POLYURETHANES

This is a division, of application Ser. No. 656,909 filed Feb. 10, 1976, now U.S. Pat. No. 4,173,567.

FIELD OF THE INVENTION

This invention relates to new organic isocyanates, to a process for their production and to their use as reactants for compounds containing isocyanate-reactive hydrogen atoms.

BACKGROUND OF THE INVENTION

German Offenlegungsschrift No. 2,329,300 relates to heterocyclic polyisocyanates obtained by reacting diisocyanates with hydrocyanic acid. In addition to hydrocyanic acid, compounds which eliminate hydrocyanic acid, such as, for example, the addition products of hydrocyanic acid with aldehydes or ketones (cyanhydrins), are also recommended as starting materials. The structure of the polyisocyanates obtained by the process according to DT-OS No. 2,329,300 is independent of whether hydrocyanic acid or the above-mentioned hydrocyanic acid derivatives are used as starting material (Example 10 of DT-OS No. 2,329,300). This discovery can be attributed to the fact that the authors of DT-OS No. 2,329,300 used reaction conditions under which the hydrocyanic acid adducts with aldehydes or ketones decomposed into their constituents, hydrocyanic acid and aldehyde or ketone, before reaction with the diisocyanate.

It has now surprisingly been found that new isocyanates having advantageous properties by comparison with the isocyanates of the above-mentioned prior art can be obtained by carrying out the reaction between diisocyanate and cyanhydrins in a first reaction stage under such mild conditions that the cyanhydrin is not decomposed into hydrocyanic acid and carbonyl compound, but instead a simple adduct of the cyanhydrin with the diisocyanate is initially formed. The action of heat on this intermediate product in the presence of excess quantities of starting diisocyanate results in the formation of new heterocyclic isocyanates corresponding to general formula (I) below (n=O, Y=—O—). These new isocyanates are distinguished from the isocyanates according to DT-OS No. 2,329,300 obtained from the corresponding starting materials in particular by their much lower viscosity and by the better lacquer properties of the polyurethane lacquers produced from them.

According to the invention it has also been found that isocyanates which are largely similar in structure and properties, and which, in particular, have valuable lacquer properties, are formed from organic diisocyanates by a similar reaction with α-aminonitriles, β-hydroxy or β-aminonitriles.

SUMMARY OF THE INVENTION

Accordingly, the present invention relates to new isocyanates corresponding to the formula:

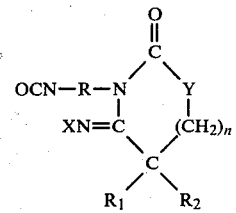

The invention also relates to a process for the production of the compounds of formula (I) wherein an organic diisocyanate corresponding to the formula:

$$OCN-R-NCO \quad (II)$$

is reacted with a compound corresponding to the formula:

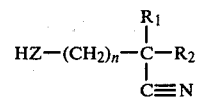

to form an adduct corresponding to the formula:

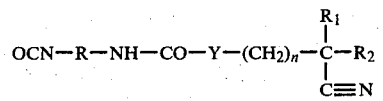

and the adduct thus formed is subsequently converted into the required end product (I) by the heating in the presence of excess quantities of the diisocyanate of formula (II).

The invention also relates to the use of the preferred polyisocyanates described in more detail below, obtainable by the process according to the invention, as reactants for compounds containing at least two isocyanate-reactive hydrogen atoms in the production of polyurethane plastics by the isocyanate polyaddition process known per se.

In the above formulae and hereinafter, R, $R_1$, $R_2$, X, Y, Z and n have the following meanings:

R represents an aliphatic hydrocarbon radical having 2 to 12 carbon atoms, a cycloaliphatic hydrocarbon radical having 4 to 15 carbon atoms, an aromatic hydrocarbon radical having 6 to 15 carbon atoms or an araliphatic hydrocarbon radical having 7 to 15 carbon atoms optionally substituted by halogen, $C_1$–$C_4$-alkyl, methoxy, nitro, and/or $C_1$–$C_4$-carbalkoxy groups. R preferably represents an aliphatic hydrocarbon radical having 4 to 8 carbon atoms or a cycloaliphatic hydrocarbon radical having 5 to 10 carbon atoms.

$R_1$ and $R_2$ are the same or different and represent hydrogen an aliphatic hydrocarbon radical having 1 to 17 carbon atoms, a cycloaliphatic hydrocarbon radical having 4 to 15 carbon atoms, an aromatic hydrocarbon radical having 6 to 15 carbon atoms or an araliphatic hydrocarbon radical having 7 to 15 carbon atoms optionally substituted by halogen, $C_1$–$C_4$-alkyl, methoxy, nitro or $C_1$–$C_4$-carbalkoxy groups, or together with the ring carbon atom form a cycloaliphatic ring having 4 to 8 carbon atoms. $R_1$ and $R_2$ preferably represent an optionally olefinically unsaturated aliphatic hydrocarbon radical having 1 to 4 carbon atoms or, together with the ring carbon atom, a cycloaliphatic hydrocarbon radical having 5 to 6 carbon atoms.

X represents hydrogen or —CO—NH—R—NCO. X preferably represents —CO—NH—R—NCO.

Y represents —O— or —N($R_3$)—, where $R_3$ is hydrogen, an aliphatic hydrocarbon radical having 1 to 4 carbon atoms, a cycloaliphatic hydrocarbon radical having 5 to 6 carbon atoms, a phenyl radical or —CO—NH—R—NCO. Y preferably represents —O—.

Z represents —O— or a radical —N($R_4$)—, where $R_4$ is hydrogen, an aliphatic hydrocarbon radical having 1 to 4 carbon atoms or a cycloaliphatic hydrocarbon radical having 5 to 6 carbon atoms or a phenyl radical. Z preferably represents —O—.

n=0 or 1, preferably 0.

DETAILED DESCRIPTION OF THE INVENTION

In the process according to the invention, diisocyanates of formula (II) are reacted with hydroxy or aminonitriles of formula (III) at a temperature in the range from about −25° C. to +200° C. and preferably at a temperature in the range from about 0° C. to 180° C., preferably in the presence of suitable catalysts. The process according to the invention may be carried out, for example, by initially introducing the reactants in admixture and initiating the reaction by adding the catalyst. However, it may also be carried out by initially introducing the diisocyanate and catalyst, followed by addition of the hydroxy or aminonitrile. The process according to the invention probably passes through an intermediate stage of formula (IV) which is cyclized at elevated temperature into compounds of formula (I) (X=H, Y=—O— or —N($R_4$)—). If desired the diisocyanates or triisocyanates (I) according to the invention, in which X represents —CO—NH—R—NCO and Y represents —O— or —N($R_3$)— ($R_3$=—CO—NH—R—NCO), are then formed by a secondary reaction with excess diisocyanate (II) with the group =NX with the group —N$R_4$— ($R_4$=H). Especially in cases where the α-hydroxy nitriles, which represent particularly preferred starting compounds (III) for the process according to the invention, are used, it is important to ensure, by careful temperature treatment at the beginning of the reaction, that the addition reaction between (II) and (III) takes place before the hydroxy nitrile (III) decomposes into its constituents HCN and

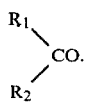

In practice, this result is achieved by carrying out the primary reaction between (II) and (III) to form the intermediate product (IV) at a temperature in the range from about −25° C. to +80° C. and preferably at a temperature in the range from about +15° C. to +25° C. It is advisable to carry out the first step of the reaction at the same temperature in those cases where α-aminonitriles are used as starting materials. The temperature of the first reaction step is, however, less critical in the case where β-hydroxynitriles or β-aminonitriles are used as starting materials. In these cases the first reaction step can be carried out within above wide range from about −25° C. to +200° C. preferably from about 0° C. to 180° C. In order subsequently to cyclize the intermediate product (IV), the reaction mixture is then heated to elevated temperatures this means to about 40° to 160° C. preferably 60° to 120° C.

In general, from about 5 to 15 mols of diisocyanate (II) are preferably used per mol of compound (III) in the process according to the invention. The primary reaction between (III) and (II) to form (IV) is over when the heat effect observed when the reactants are combined with the catalyst abates. The end of the cyclization reaction is indicated by the disappearance of the nitrile edge in the infra red spectrum.

If desired, unreacted diisocyanate may be removed on completion of the reaction, for example, by thin-layer or rotary distillation or by extraction with solvents, for example, cyclohexane, hexane or petroleum ether. However, the solutions of the new polyisocyanates in the diisocyanates used as starting compounds, obtainable in the process according to the invention, are also suitable for numerous applications which are mentioned in more detail hereinafter. As already mentioned, the formation of diisocyanates corresponding to the above general formula may be controlled by varying temperature. The formation of triisocyanates is possible not only in cases where Y=—NH, but may also be obtained in cases where Y=—O— by a secondary reaction, i.e. by reacting the excess diisocyanate used as starting material with the diisocyanate according to the invention (reaction of the diisocyanate with the group —CO—N$\underline{H}$—R—). In addition, heating the reaction mixture to elevated temperatures for several hours results in the formation of mixtures which, in addition to diisocyanates and triisocyanates, contain homologues of higher molecular weight. At elevated temperatures, polyisocyanates containing uretdione, biuret or isocyanurate groups can also be expected to be formed in addition to the homologues of higher molecular weight. In the formation of these secondary products is undesirable, it is advisable to carry out the process according to the invention at low temperatures in the range from about 0° C. to 80° C., in which case the reaction mixture is heated to this temperature for about 30 to 120 minutes. monoisocyanates are formed if the reaction temperature is kept below 80° C. Above secondary reaction leading to di- and triisocyanates take place at temperatures of above 80° C. as e.g. 80°–200° C. The degree of diisocyanate and/or triisocyanate formation by said secondary reactions can be determined by controlling the NCO-content of the reaction mixture.

Providing these precautionary measures are taken, removal of the excess starting diisocyanate leaves and products of which at least about 70% and preferably at least about 90% consist of the mono-, di- and tri-isocyanates corresponding to general formula (I) above.

The catalysts used, which are mentioned hereinafter, may generally remain in the reaction products without any adverse effect upon the stability of the end products in storage. In cases where the catalysts used in accordance with the invention are harmful in the production of plant protection agents, PU-plastics, PU-lacquers and PU-films, they are removed by filtration, centrifuging or decanting (insoluble catalysts) or are deactivated by alkylation, acylation or salt formation.

Any organic diisocyanates corresponding to the general formula R(NCO)$_2$, where R is as defined above, may be used in the process according to the invention. Preferred aliphatic or cycloaliphatic diisocyanates are, for example, tetramethylene diisocyanate, pentamethylene diisocyanate, hexamethylene diisocyanate, 1,3-cyclopentylene diisocyanate, 1,4-cyclohexylene diisocyanate, 1,2-cyclohexylene diisocyanate, hexahydroxylylene diisocyanate, 4,4'-dicyclohexyl diisocyanate, 1,2-di-(isocyanatomethyl)-cyclobutane, 1,3-bis-(isocyanatopropyl)-2-methyl-2-propyl propane, 1-methyl-2,4-diisocyanatocyclohexane, 1-methyl-2,6-diisocyanatocyclohexane, bis-(4-isocyanatocyclohexyl)-methane, 1,4-diisocyanatocyclohexane and 1,3-diisocyanatocyclohexane or 3,3,5-trimethyl-5-isocyanatomethyl cyclohexyl isocyanate ("isophorone diisocyanate"). In addition to aliphatic and cycloaliphatic diisocyanates of this kind, it is also possible in the process according to the invention to use aromatic diisocyanates such as, for example, 2,4-diisocyanatotoluene, 2,6-diisocyanatotoluene or 4,4'-diisocyanatodiphenyl methane, araliphatic diisocyanates, such as m- or p-xylylene diisocyanate, or diisocyanates containing ester groups such as 2,6-diisocyanato caproic acid esters, β-isocyanatoethyl esters and γ-isocyanatopropyl esters of isocyanato caproic acid.

Hydroxy and aminonitriles (III) suitable for use in the process according to the invention are the following:

(1) α-hydroxy nitriles such as, for example, the cyanhydrins of formaldehyde, acetaldehyde, propionaldehyde, butyraldehyde, isobutyraldehyde, acetone, methylethyl ketone, isopropyl methyl ketone, monochloracetone, benzaldehyde, o-nitrobenzaldehyde, m-nitrobenzaldehyde, p-nitrobenzaldehyde, o-chlorobenzaldehyde, m-chlorobenzaldehyde, p-chlorobenzaldehyde, o-methoxy benzaldehyde, p-methoxy benzaldehyde, m-methyl benzaldehyde, p-methyl benzaldehyde, benzyl methyl ketone, β-phenyl ethyl ketone, β-phenyl propyl ketone, cyclopentanone, cyclohexanone, isopropyl phenyl ketone, cyclohexyl phenyl ketone, 2-methyl cyclohexanone, 3-methyl cyclohexanone, 4-methyl cyclohexanone, cycloheptanone, chloral, acrolein, crotonaldehyde and acetoacetic acid ethyl ester.

(2) α-aminonitriles such as, for example, α-aminoacetonitrile, α-aminopropionitrile, α-amino-α-methyl propionitrile, α-(N-methyl amino)-propionitrile, α-aminobutyronitrile, α-aminoisobutyronitrile, α-amino-α-methyl propionic acid nitrile, α-amino-α-methyl isobutyronitrile, α-methyl aminoisobutyronitrile, α-butyl aminoisobutyronitrile, α-cyclohexyl aminoisobutyronitrile, α-phenyl aminoisobutyronitrile, α-1-cyclohexyl amino-1-cyanocyclohexane and (α-amino-α-phenyl acetic acid nitrile).

(3) β-hydroxy nitriles such as, for example, β-hydroxy propionitrile, β-hydroxy-α-methyl propionitrile, β-hydroxy-β-methyl propionitrile, β-hydroxy-β-cyclohexyl propionitrile and β-hydroxy-β-phenyl propionitrile.

(4) β-aminonitriles such as, for example, β-aminopropionitrile, β-methyl aminopropionitrile, β-hexyl aminopropionitrile, β-cyclohexyl aminopropionitrile, β-amino-α-methyl propionitrile and β-methyl amino-β-methyl propionitrile.

It is, of course, also possible in the process according to the invention to use any mixtures of the compounds (III) mentioned by way of example in (1) to (4) above, more especially for controlling the service properties of the end products. The cyanhydrins of the unsubstituted aliphatic or cycloaliphatic aldehydes or ketones mentioned in (1) above are particularly preferred for the process according to the invention.

Compounds accelerating the isocyanate polyaddition reaction, known per se from polyurethane chemistry, are used as catalysts in the process according to the invention. Compounds of this kind are, in particular, tertiary amines such as, for example, triethyl amine, diaza-bicyclo-(2,2,2)-octane, 1,5-diaza-bicyclo-(4,3,0)-non-5-ene, 1,8-diaza-bicyclo-(5,4,0)-undec-7-ene, dimethyl aniline, dimethyl benzyl amine, pyridine, 2-, 3-, 4-picoline, N,N-diethyl aniline, quinoline, N-methyl piperidine, N-methyl dicyclohexyl amine, N,N-dimethyl cyclohexyl amine, N-cyclohexyl piperidine, N-cyclohexyl morpholine and 2,6-, 2,4-lutidine; organic zinc compounds, such as, for example, those of 2-ethyl caproic acid, organic tin compounds such as, for example, dibutyl tin dilaurate, bis-(tributyl tin)-oxide, dibutyl tin-bis-(2-ethyl hexoate) or tetrabutyl tin. Other suitable catalysts are lead compounds, such as, trimethyl lead acetate or N-(tri-n-butyl lead)-imidazole or phosphorus compounds, such as, triphenyl phosphine or tributyl phosphine, and basic salts of hydrocyanic acid, such as sodium cyanide or potassium cyanide. The catalysts mentioned by way of example are used in quantities of from about 0.01 to 3 mol % and preferably in quantities of from about 0.05 to 1 mol %, based on compound (III), in the process according to the invention. Further suitable catalysts are disclosed in Polyurethanes: Chemistry and Technology, Part I, by Saunders and Frisch, Interscience Publishers, 1964.

The process according to the invention may be carried out either in the absence or even in the presence of an inert organic solvent. Suitable inert solvents are, for example, aliphatic and cycloaliphatic hydrocarbons, halogencontaining hydrocarbons such as methylene chloride, chloroform, di- and tri-chlorethylene, aromatic hydrocarbons, such as benzene, toluene, xylene, halogenated aromatic hydrocarbons such as chlorobenzene, dichlorobenzene, and trichlorobenzene, dioxane, ethyl acetate, ethyl glycol acetate, acetone, acetonitrile, dimethyl formamide and mixtures of these solvents.

The polyisocyanates (I) according to the invention represent a new class of organic polyisocyanates. The fact that they are compounds having the general structure indicated above is apparent from molecular weight determination and from infrared (Makromol. Chem. 78, 191 (1964), nuclear resonance and mass spectroscopic data. The new compounds are suitable for use as intermediate products in the production of plant-protection agents and in particular represent valuable starting materials for the production of polyurethane plastics. In particular, the polyisocyanates according to the invention having aliphatically bound isocyanate groups are valuable starting materials for the production of light-stable polyurethane lacquers and films. The new polyisocyanates are readily soluble in conventional lacquer solvents and are highly compatible with pigments. They are particularly suitable for low-solvent lacquer systems owing to their low viscosity. Their greatly reduced vapor pressure by comparison with the corresponding diisocyanates used as starting materials, and their resulting physiological acceptability, are of considerable practical significance.

EXAMPLE 1

2016 g of hexamethylene diisocyanate (12 mols) and 1 ml of triethyl amine are initially introduced into a three-necked flask, followed by the dropwise addition over a period of 30 minutes at room temperature of 68.4 g of glycol nitrile (1.2 mols). The mixture is then slowly heated to 160° C. and, after 10 minutes at that temperature, is cooled to room temperature. The catalyst is destroyed by means of benzoyl chloride and the reaction product freed from excess hexamethyl diisocyanate by thin-layer distillation.

Yield: 530 g of a diisocyanate having the following idealized structure:

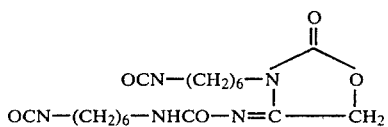

NCO found: 21.3%
NCO calculated: 21.4%
$\eta_{25°}$ C.: 440 cP
Analysis: calculated: C 54.95, H 6.92, N 17.80, O 20.33. found: C 55.1, H 7.00, N 18.1, O 20.3.

EXAMPLE 2

2523 g of hexamethylene diisocyanate (15 mols) are reacted with 157 g of isobutyraldehyde cyanhydrin (1.5 mols) in the presence of 2 g of diaza-bicyclo-(2,2,2)-octane in the same way as in Example 1. Removal of the excess hexamethylene diisocyanate by extraction with cyclohexane leaves 772 g of a diisocyanate having the following idealized structure:

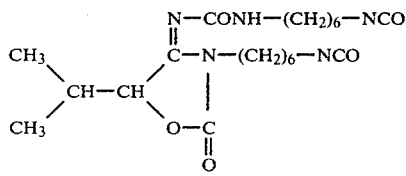

$\eta_{25°}$ C.: 2080 cP
NCO calculated: 19.3%
NCO found: 19.1%
Analysis: calculated: C 57.91, H 7.64, N 16.08, O 18.37. found: C 57.8, H 7.7, N 16.3, O 13.3.

EXAMPLE 3

53 g (0.5 mol) of benzaldehyde (freshly distilled) and 0.5 ml of triethylamine are combined in a stirrer-equipped vessel and 20 ml of hydrocyanic acid (0.5 mol) added dropwise at such a rate that the temperature does not exceed 40° C. After stirring for 60 minutes at room temperature, 841 g of hexamethylene diisocyanate (5 mols) and 0.5 ml of the zinc(II)salt of 2-ethyl caproic acid are added. The further procedure is then as described in Example 1.

Removal of the monomer leaves 180 g of a diisocyanate having the following idealized structure:

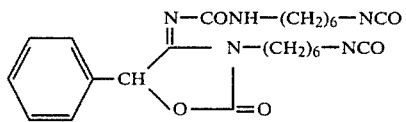

$\eta_{25°}$ C.: 1050 cP
NCO found: 17.5%
NCO calculated: 17.92%
Analysis: calculated: C 61.39, H 6.66, N 14.92, O 17.04. found: C 60.9, H 6.5, N 14.9, O 17.0.

EXAMPLE 4

841 g of hexamethylene diisocyanate (5 mols) are reacted with 41.5 g of acrolein cyanhydrin (0.5 mol) in the presence of 0.5 ml of quinoline and 1 g of pyrocatechol in the same way as in Example 1. The reaction mixture obtained is subject to thin-layer distillation twice at 180° C. in an oil pump vacuum.

Yield: 190 g of a diisocyanate having the following idealized structure:

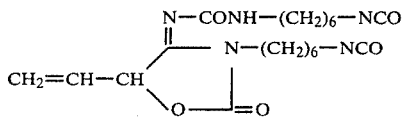

$\eta_{25°}$ C.: 715 cP
NCO calculated: 20.0%
NCO found: 19.9%
Analysis: calculated: C 57.26, H 6.97, N 16.70, O 19.07. found: C 57.2, H 7.2, N 16.7, O 19.3.

EXAMPLE 5

3360 g of hexamethylene diisocyanate (20 mols), 186.9 g of cyclohexanone cyanhydrin (1.5 mols), 1 ml of tin octoate and 1 ml of triethyl amine, are reacted as described in Example 1. Removal of the monomer leaves 782 g of a polyisocyanate having the following idealized structure:

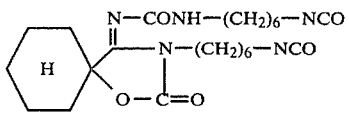

$\eta_{25°}$ C.: 1770 cP
NCO calculated: 18.2%
NCO found: 17.9%
Analysis: calculated: C 59.85, H 7.64, N 15.17, O 17.33. found: C 59.8, H 7.8, N 15.4, O 17.3.

EXAMPLE 6

3364 g of hexamethylene diisocyanate (20 mols) and 2 mols of acetaldehyde cyanhydrin (142 g) are mixed under nitrogen in a 5 liter capacity stirrer-equipped apparatus. Following the addition of 1 ml of zinc octoate, a weakly exothermic reaction begins, being over after 30 minutes. Following the addition of 1 ml of triethyl amine, the mixture is stirred for 15 minutes at room temperature, quickly heated to 160° C. and kept at that temperature for 15 minutes. The reaction mixture is freed from excess hexamethylene diisocyanate by thin-layer distillation.

Yield: 952 g of a polyisocyanate having the following idealized structure:

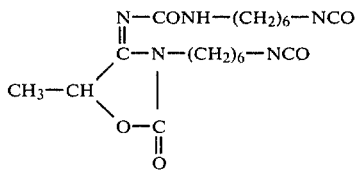

$\eta_{25°}$ C.: 480 cP
NCO calculated: 20.6%

NCO found: 20.3%

Analysis: calculated: C 56.0, H 7.17, N 17.09, O 19.63. found: C 55.8, H 7.3, N 17.0, O 20.0.

EXAMPLE 7

2523 g of hexamethylene diisocyanate (15 mols) and 127 g of propionaldehyde cyanhydrin are reacted in the presence of 1 ml of zinc octoate and 1 ml of triethylamine in the same way as described in Example 6.

Yield: 821 g of polyisocyanate having the following idealized structure:

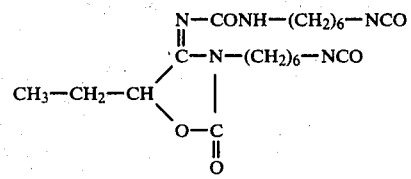

$\eta_{25°}$ C.: 720 cP
NCO calculated: 19.95%
NCO found: 19.7%

Analysis: calculated: C 56.99, H 7.41, N 16.62, O 18.98. found: C 56.7, H 7.2, N 16.8, O 19.0.

EXAMPLE 8

841 g of hexamethylene diisocyanate (5 mols) are mixed at room temperature with 78.5 g of acetoacetic ester cyanhydrin (0.5 mol), 0.5 ml of zinc octoate and 0.5 ml of triethylamine in a stirrer-equipped vessel. The mixture is then heated for 10 minutes to 160° C. and the catalyst neutralized with 0.5 ml of acetyl chloride. The reaction product is subjected to thin-layer distillation twice at 180° C. in an oil pump vacuum and all but 0.1% of the monomer, (hexamethylene diisocyanate), removed.

Yield: 195 g of a polyisocyanate having the following idealized structure:

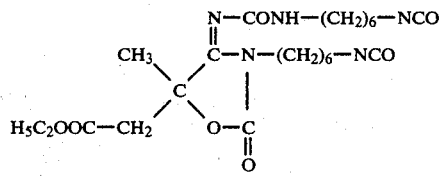

$\eta_{25°}$ C.: 5200 cP
NCO calculated: 17.05%
NCO found: 16.8%

Analysis: calculated: C 55.97, H 7.15, N 14.19, O 22.69. found: C 55.7, H 6.93, N 14.5, O 22.8.

EXAMPLE 9

42.5 g of acetone cyanhydrin (0.5 mol) and 0.5 g of diazabicyclo-(2,2,2)-octane are added to 1250 g of 4,4'-di-isocyanatodiphenyl methane (5 mols), followed by heating for 60 minutes to 160° C. After 30 minutes at that temperature, the reaction mixture is left to cool. 1240 g of a polyisocyanate having the following idealized structure:

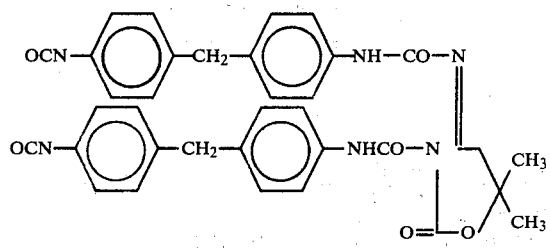

in 3 mols of 4,4'-diisocyanatodiphenyl methane are obtained. The monomer-free polyisocyanate may be freed from the monomer by extraction.

NCO calculated: 14.86%
NCO found: 14.5%

Analysis: calculated: C 69.73, H 4.65, N 11.96, O 13.66. found: C 69.5, H 4.4, N 12.1, O 13.8.

EXAMPLE 10

870 g of 2,4-diisocyanatotoluene (5 mols) are combined while stirring in a reaction vessel with 0.5 g of 1,5-diazabicyclo-(4,3,0)-non-5-ene, 0.5 g of dibutyl tin dilaurate and 42.5 g of acetone cyanhydrin (0.5 mol), followed by heating for 2 hours to 150° C. After another 30 minutes, the reaction mixture is left to cool and, providing the reaction mixture is not directly used for further reactions, is extracted with cyclohexane until the monomer has been removed. 285 g of a polyisocyanate having the following idealized structure:

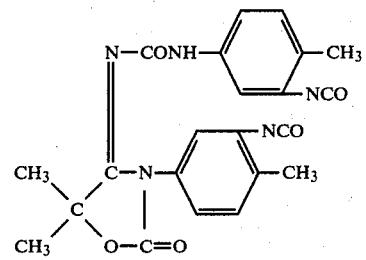

in the form of a white solid melting at approximately 195° C. are obtained.

NCO calculated: 19.4%
NCO found: 19.1%

Analysis: calculated: C 60.96, H 4.42, N 16.16, O 18.46. found: C 60.7, H 4.6, N 16.3, O 18.2.

EXAMPLE 11

841 g of hexamethylene diisocyanate (5 mols), 50 g of methyl ethyl ketone cyanhydrin, 0.5 g of triethylamine and 0.5 ml of zinc octoate are reacted in the same way as described in Example 1. On cooling, the triethylamine is blocked by the addition of 0.6 g of p-toluene sulphonic acid chloride.

The mixture is introduced cold into the thin-layer distillation apparatus in which it is subjected to thin-layer distillation at 180° to 185° C./0.05 Torr (oil pump).

Yield: 218 g of a polyisocyanate having the following idealized structure:

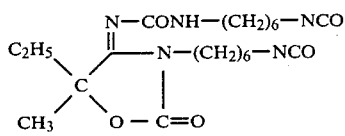

η₂₅° C.: 3200 cP
NCO calculated: 19.3%
NCO found: 19.5%
Analysis: calculated: C 57.91, H 7.64, N 16.08, O 18.34. found: C 58.2, H 7.81, N 15.9, O 18.1.

EXAMPLE 12

In a stirrer-equipped apparatus, 20 ml of hydrocyanic acid (0.5 mol) are added to 85 g (0.5 mol) of undecanone-(2) in the presence of 0.5 ml of triethylamine, followed by stirring for 30 minutes at 40° C. 841 g of hexamethylene diisocyanate (5 mols) and 0.5 ml of tin octoate are introduced into the cooled mixture. After heating for 60 minutes to 160° C., the mixture is stirred for 30 minutes at that temperature. After cooling, a polyisocyanate having the following idealized structure can be isolated by thin layer distillation in a yield of 293 g:

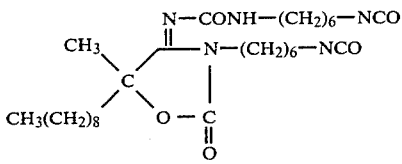

η₂₅° C.: 3650 cP
NCO calculated: 15.75%
NCO found: 16.1%
Analysis: calculated: C 63.01, H 8.88, N 13.12, O 14.99. found: C 63.2, H 8.91, N 13.1, O 14.7.

EXAMPLE 13

Following the procedure described in Example 1, 3364 g of hexamethylene diisocyanate (20 mols) and 170 g of acetone cyanhydrin (2 mols) are mixed with catalytic quantities of zinc octoate and triethylamine and, after the exothermic reaction has abated, the reaction mixture is heated to 160° C. and kept at that temperature for 10 minutes. The cooled reaction mixture can be obtained free from monomer by countercurrent extraction in a column with cyclohexane or petroleum ether.

Yield: 1042 g of a polyisocyanate having the following idealized structure:

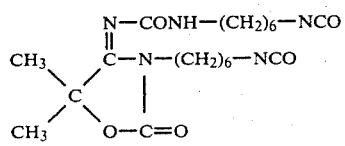

η₂₅° C.: 1720 cP
NCO calculated: 19.9%
NCO found: 19.6%
Analysis: calculated: C 56.99, H 7.41, N 16.62, O 18.98. found: C 57.1, H 7.12, N 16.9, O 18.7.

EXAMPLE 14

Following the procedure of Example 1, 222 g of isophorone diisocyanate (1 mol), 8.5 g of acetone cyanhydrin (0.1 mol), 0.1 mol of zinc octoate and 0.1 ml of triethylamine are heated for 1 hour to 160° C. and subsequently subjected to thin-layer distillation at 180° C./0.2 Torr. 47 g of a resin-like polyisocyanate having the following idealized structure are obtained:

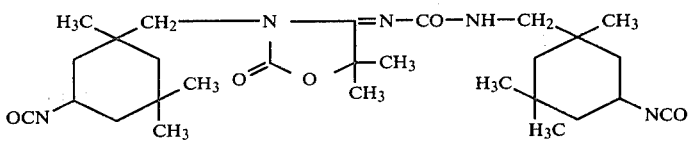

NCO calculated: 15.9%
NCO found: 15.7%
Analysis: calculated: C 63.49, H 8.18, N 13.22, O 15.10. found: C 63.2, H 8.0, N 13.4, O 15.3.

EXAMPLE 15

673 g of hexamethylene diisocyanate (4 mols) and 174 g of 2,4-diisocyanatotoluene (1 mol) are reacted with 42.5 g of acetone cyanhydrin (0.5 mol) in the presence of 0.5 ml of triethylamine. After the weakly exothermic reaction has abated, the reaction mixture is heated for 1 hour to 160° C. A clear, low-viscosity reaction product is obtained after cooling and may be freed from the monomer by extraction with ether. The monomer-free polyisocyanate has the following idealized structure:

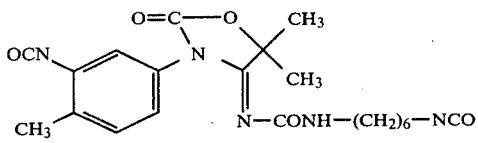

NCO calculated: 19.65%
NCO found: 19.3%
Analysis: calculated: C 59.0, H 5.90, N 16.39, O 18.72. found: C 58.8, H 5.81, N 16.40, O 18.8.

EXAMPLE 16

841 g of hexamethylene diisocyanate (5 mols) are reacted with 42.5 g of acetone cyanhydrin (0.5 mol) in the presence of 0.2 ml of triethylamine and 0.2 ml of zinc octoate by stirring the reaction mixture for 3 hours at 70° C. The unreacted hexamethylene diisocyanate is then removed from the reaction product by extraction with petroleum ether. 130 g of a reaction product essentially consisting of a monoisocyanate having the following idealized structure are obtained:

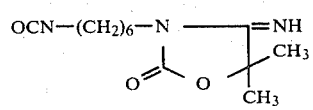

NCO calculated: 16.6%

NCO found: 16.9%
Analysis: calculated: C 56.90, H 7.56, N 16.59, O 18.95. found: C 57.0, H 7.71, N 16.3, O 18.8.

EXAMPLE 17

In a stirrer-equipped apparatus, 336 g of hexamethylene diisocyanate (2 mols) are reacted for 2 hours at 40° C. with 21.3 g of acetaldehyde cyanhydrin (0.3 mol). 0.1 g of diaza-bicyclo-(2,2,2)-octane and 0.01 g of tin octoate are used as catalyst. The reaction product is obtained free from monomer by extraction with cyclohexane/petroleum ether. 75 g of a reaction product essentially consisting of a monoisocyanate having the following idealized structure are obtained:

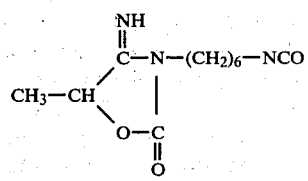

NCO calculated: 17.6%
NCO found: 17.9%
Analysis: calculated: C 55.21, H 7.16, N 17.56, O 20.06. found: C 55.30, H 7.42, N 17.3, O 19.7.

EXAMPLE 18

To prepare a lacquer, 154 parts by weight of a polyester, prepared from phthalic acid anhydride and trimethylol propane, OH-number 260, in the form of a 65% solution in ethyl glycol acetate, 8.40 parts by weight of zinc octoate (8% of Zn) in the form of a 10% solution in xylene, 105.30 parts by weight of titanium dioxide and 141.80 parts by weight of ethyl glycol acetate, are mixed with 110.50 parts by weight of the polyisocyanate of Example 5.

The mixture has a viscosity of about 25 seconds, as determined in a 4 mm DIN cup (DIN 53 211). This viscosity makes the mixture suitable for spraying, although it may be adjusted to the required level by adding, or reducing the quantity of, ethyl glycol acetate. This lacquer mixture has a processing time of 2 hours. Properties of the lacquer film: 7.5 mm Erichsen indentation DIN 53 156, pendulum hardness (according to Konig) DIN 53 157, 218 seconds. The lacquer is dried for 30 minutes at 120° C.

EXAMPLE 19

To prepare a lacquer, 154 parts by weight of a 65% solution of a polyester prepared from phthalic acid and trimethylol propane (8% OH) in ethyl glycol acetate, 8 parts by weight of zinc octoate (8% of Zn) in the form of a 10% solution in xylene, 100.1 parts by weight of titanium dioxide and 119.8 parts of ethyl glycol acetate, are mixed with 100.1 parts by weight of the polyisocyanate of Example 6.

The lacquer thus prepared has a viscosity of 25 seconds, as measured in a 4 mm DIN cup (DIN 53 211), for a solids content of 62.3%. The viscosity may be adjusted by the quantity of ethyl glycol acetate used for roll coating, two-component hot spraying or for conventional spread-coating and spray-coating techniques. The lacquer has a processing time of about 5 hours. The lacquer is dried for up to 30 minutes at 120° C.
Properties of the lacquer film:
Erichsen indentation DIN 53 156 8 mm
pendulum hardness (according to Konig) DIN 53 157 - 210 seconds.

EXAMPLE 20

In a 1.5 liter capacity stirrer-equipped apparatus, 1682 g of hexamethylene diisocyanate (10 mols) and 84 g of α-aminoisobutyronitrile (1 mol) are slowly heated to 160° C. in the presence of 1 ml of triethylamine. After stirring for 10 minutes at that temperature, the excess hexamethylene diisocyanate is removed by thin-layer distillation at 180° C./0.2 Torr.

577 g of a polyisocyanate having the following idealized structure are obtained:

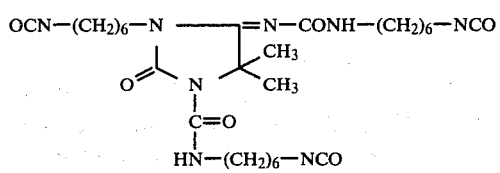

$\eta_{25°\ C.}$: 11,320 cP
NCO calculated: 21.4%, found: 21.6%.

EXAMPLE 21

2523 g of hexamethylene diisocyanate (15 mols) and 126 g of α-aminoisobutyronitrile (1.5 mols) are reacted with one another in the same way as described in Example 20, but in the absence of a catalyst. Thin-layer distillation gives 603 g of a reaction product having the following idealized structure:

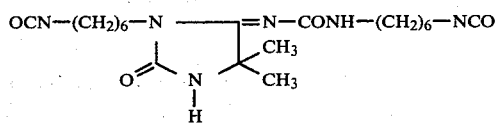

$\eta_{25°\ C.}$: 5850 cP
NCO calculated: 20.0%, found: 20.1%

EXAMPLE 22

98 g of β-methyl aminoisobutyronitrile (1 mol) are added dropwise at 40° C. to 1680 g of hexamethylene diisocyanate (10 mols). After the exothermic reaction has abated, the reaction mixture is briefly heated to 160° C. and, after cooling, is subjected to thin-layer distillation at 180° C./0.2 Torr in order to remove the monomeric hexamethylene diisocyanate. 430 g of a polyisocyanate having the following idealized structure are obtained:

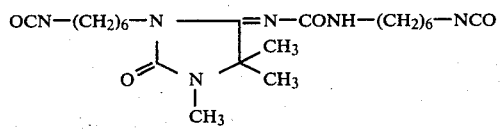

$\eta_{25°\ C.}$: 15,400 cP
NCO calculated: 19.3%, found: 18.8%

EXAMPLE 23

11.2 g of α-ethyl aminoisobutyronitrile (0.1 mol), containing 0.1 ml of triethylamine and 0.1 ml of zinc octoate, are added dropwise at room temperature to 168 g of hexamethylene diisocyanate (1 mol). After the exothermic reaction has abated, the mixture is briefly heated to 140° C. and subsequently subjected to thin-layer distillation at 170° C./0.1 Torr. 41 g of polyisocyanate having the following idealized structure are obtained:

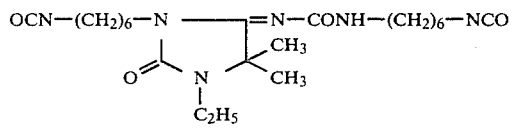

$\eta_{25° C.}$: 21,200 cP
NCO calculated: 18.7%, found: 18.4%.

EXAMPLE 24

840 g of hexamethylene diisocyanate (5 mols) and 62 g of 1-amino-1-cyanocyclohexane are reacted in the same way as described in Example 21 and the reaction product freed from the excess monomer by thin-layer distillation. 218 g of a polyisocyanate having the following idealized structure are obtained:

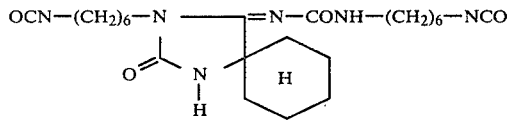

$\eta_{25° C.}$: 16,700 cP
NCO calculated: 18.2%, found: 18.4%.

EXAMPLE 25

840 g of hexamethylene diisocyanate (5 mols) and 69 g of 1-methyl amino-1-cyanocyclohexane (0.5 mol) are mixed and, after the exothermic reaction has abated, briefly heated to 150° C. After cooling, the excess hexamethylene diisocyanate is removed by repeated extraction with cyclohexane. 225 g of a polyisocyanate having the following idealized structure are obtained:

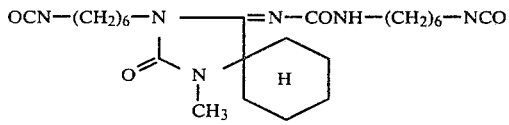

$\eta_{25° C.}$: 25,000 cP
NCO calculated: 17.7%, found: 17.3%.

EXAMPLE 26

0.1 ml of triethylamine and 0.1 ml of zinc octoate are added to 840 g of hexamethylene diisocyanate (5 mols), followed by the gradual dropwise addition at room temperature 103 g of 1-cyclohexyl amino-1-cyanocyclohexane (0.5 mol). After the exothermic reaction has abated, the reaction mixture is heated for 10 minutes to 160° C., followed by the addition of 0.5 ml of benzoyl chloride. After cooling, the reaction product is extracted with cyclohexane and petroleum ether. 253 g of a polyisocyanate having the following idealized structure are obtained:

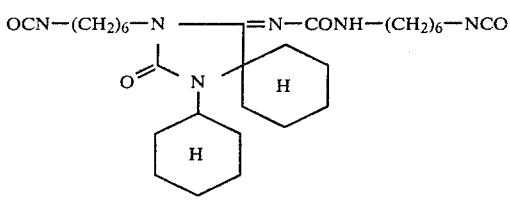

$\eta_{25° C.}$: 34,000 cP
NCO calculated: 15.5%, found: 16.0%.

EXAMPLE 27

1680 g of hexamethylene diisocyanate (10 mols) are introduced into a 3 liter capacity three-necked flask, followed by the dropwise addition over a period of 30 minutes of 84 g of 3-methyl aminopropionitrile. The internal temperature rises to 52° C. After the exothermic reaction has abated, 1 g of diazabicyclooctane and 1 ml of zinc octoate are introduced into the reaction mixture, followed by heating for 1 hour to 160° C. Removal of the monomeric hexamethylene diisocyanate by thin-layer distillation gives 380 g of a polyisocyanate having the following idealized structure:

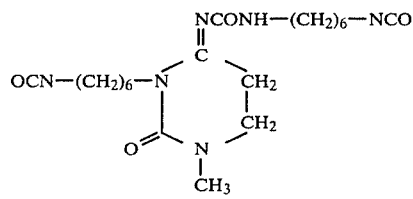

$\eta_{25° C.}$: 1950 cP
NCO calculated: 20%, found: 19.6%.

EXAMPLE 28

841 g of hexamethylene diisocyanate (5 mols) are reacted with 35.5 g of β-aminopropionitrile (0.5 mol) in the same way as described in Example 27. 329 g of a polyisocyanate having the following idealized structure are obtained by way of the urea stage:

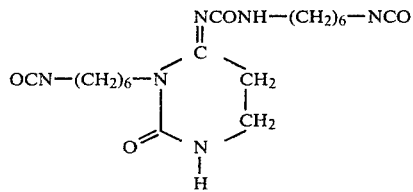

$\eta_{25° C.}$: 3852 cP
NCO calculated: 20.7%, found: 20.4%.

EXAMPLE 29

504 g of hexamethylene diisocyanate (3 mols) are reacted with 46.8 g of N-cyanoethyl aminoacetic acid ethyl ester (0.3 mol) in the same way as described in Example 27. Before thin-layer distillation, the catalysts are blocked by the addition of 0.5 ml of acetyl chloride. 150 g of a polyisocyanate having the following idealized structure are obtained.

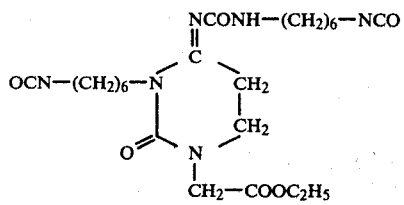

$\eta_{25°C}$: 460 cP

NCO calculated: 17.6%, found: 17.4%.

It is to be understood that any of the components and conditions mentioned as suitable herein can be substituted for its counterpart in the foregoing examples and that although the invention has been described in considerable detail in the foregoing, such detail is solely for the purpose of illustration. Variations can be made in the invention by those skilled in the art without departing from the spirit and scope of the invention except as it may be limited by the claims.

What is claimed is:

1. A process for the production of polyurethanes or of polyurethane lacquers comprising
reacting a compound containing at least two isocyanate-reactive hydrogen atoms with an organic diisocyanate of the formula

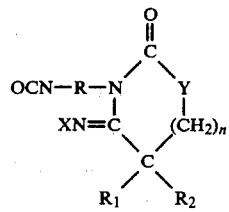 (I)

in which
R represents a substituted or unsubstituted aliphatic hydrocarbon group having 2 to 12 carbon atoms, a substituted or unsubstituted cycloaliphatic hydrocarbon group having 4 to 15 carbon atoms, a substituted or unsubstituted aromatic hydrocarbon group having 6 to 15 carbon atoms or a substituted or unsubstituted araliphatic hydrocarbon group having 7 to 15 carbon atoms, said hydrocarbon group having at most three substituents selected from the group consisting of halogen, $C_1$-$C_4$—alkyl, methoxy, nitro and $C_1$-$C_4$-carbalkoxy groups,
represents —O— or —N($R_3$)—, where $R_3$ represents hydrogen, an aliphatic hydrocarbon group having 1 to 4 carbon atoms, a cycloaliphatic hydrocarbon group having 5 to 6 carbon atoms, a phenyl group or —CO—NH—R—NCO, n=0 or 1, $R_1$ and $R_2$ are the same or different and represent hydrogen, a substituted or unsubstituted aliphatic hydrocarbon group having 1 to 17 carbon atoms, a substituted or unsubstituted cycloaliphatic hydrocarbon group having 4 to 15 carbon atoms, a substituted or unsubstituted aromatic hydrocarbon group having 6 to 15 carbon atoms or a substituted or unsubstituted araliphatic hydrocarbon group having 7 to 15 carbon atoms, said hydrocarbon group having at most three substituents selected from the group consisting of halogen, $C_1$-$C_4$-alkyl, methoxy, nitro and $C_1$-$C_4$-carbalkoxy groups or $R_1$ or $R_2$ together with the ring carbon atom form a cycloaliphatic ring having 4 to 15 carbon atoms, and represents —CO—NH—R—NCO.

2. The process according to claim 1 wherein the compound containing at least two isocyanate-reactive hydrogen atoms is a hydroxy polyester.

3. The process for the production of polyurethane lacquers according to claims 1 or 2 wherein the reaction is carried out in the presence of an inert organic solvent.

4. The process according to claims 1 or 2 wherein pigmenting agents are added during the production of the polyurethane lacquers.

* * * * *